United States Patent
Oldham et al.

(10) Patent No.: US 10,180,428 B2
(45) Date of Patent: Jan. 15, 2019

(54) SYSTEMS AND METHODS FOR ELECTRONIC DETECTION WITH NANOFETS

(71) Applicant: APPLIED BIOSYSTEMS LLC, Carlsbad, CA (US)

(72) Inventors: Mark F. Oldham, Emerald Hills, CA (US); Eric S. Nordman, Palo Alto, CA (US)

(73) Assignee: APPLIED BIOSYSTEMS, LLC, Carlsbad, CA (US)

(*) Notice: Subject to any disclaimer, the term of this patent is extended or adjusted under 35 U.S.C. 154(b) by 460 days.

(21) Appl. No.: 14/864,372

(22) Filed: Sep. 24, 2015

(65) Prior Publication Data

US 2016/0011186 A1    Jan. 14, 2016

Related U.S. Application Data

(63) Continuation of application No. 12/165,379, filed on Jun. 30, 2008, now Pat. No. 9,151,751.

(60) Provisional application No. 60/947,247, filed on Jun. 29, 2007.

(51) Int. Cl.
| | |
|---|---|
| *G01N 27/414* | (2006.01) |
| *G01N 33/543* | (2006.01) |
| *B82Y 15/00* | (2011.01) |
| *C12Q 1/6825* | (2018.01) |

(52) U.S. Cl.
CPC ........ *G01N 33/54373* (2013.01); *B82Y 15/00* (2013.01); *C12Q 1/6825* (2013.01); *G01N 27/4145* (2013.01); *G01N 27/4146* (2013.01)

(58) Field of Classification Search
None
See application file for complete search history.

(56) References Cited

U.S. PATENT DOCUMENTS

| | | | |
|---|---|---|---|
| 6,592,821 B1 | 7/2003 | Wada et al. | |
| 7,145,019 B2 | 12/2006 | Olejnik et al. | |
| 7,695,907 B2 | 4/2010 | Miyahara et al. | |
| 2002/0015954 A1 | 2/2002 | Singh et al. | |

(Continued)

FOREIGN PATENT DOCUMENTS

| | | |
|---|---|---|
| WO | 2002/31481 | 4/2002 |
| WO | 2003/021010 | 3/2003 |

(Continued)

OTHER PUBLICATIONS

Extended Search Report for European Application No. EP08796064.7, dated Mar. 14, 2014, 12 pages.

(Continued)

*Primary Examiner* — Erik B Crawford

(57) ABSTRACT

There is disclosed a system for electrical charge detection comprising a nanoFET device. Also disclosed is a method of electrical charge detection for single molecule sequencing. The method includes attaching a macromolecule or assemblies thereof to a gate of a nanoFET device and flowing in a solution of charge tags, where a charge tag includes a nucleotide attached to a charge complex. The method also includes incorporating one charge tag into the macromolecule or assemblies thereof and cleaving the charge tags from the macromolecule or assemblies thereof. The method further includes detecting at least one of current and voltage from the nanoFET device.

19 Claims, 6 Drawing Sheets

(56) References Cited

U.S. PATENT DOCUMENTS

| | | |
|---|---|---|
| 2002/0039738 A1 | 4/2002 | Williams et al. |
| 2002/0128234 A1 | 9/2002 | Hubbell et al. |
| 2003/0102510 A1 | 6/2003 | Lim et al. |
| 2003/0104386 A1 | 6/2003 | Kuhr et al. |
| 2003/0141189 A1 | 7/2003 | Lee et al. |
| 2004/0115694 A1 | 6/2004 | Van Ness et al. |
| 2004/0252867 A1 | 12/2004 | Lan et al. |
| 2004/0262636 A1 | 12/2004 | Yang et al. |
| 2005/0040483 A1 | 2/2005 | Offenhauser et al. |
| 2005/0085630 A1 | 4/2005 | Olejnik et al. |
| 2005/0106587 A1 | 5/2005 | Klapproth et al. |
| 2005/0136466 A1 | 6/2005 | Miles et al. |
| 2005/0224346 A1* | 10/2005 | Holm-Kennedy ..... B82Y 30/00 204/403.01 |
| 2005/0244954 A1* | 11/2005 | Blackburn ........ B01L 3/502753 435/287.2 |
| 2005/0266403 A9 | 12/2005 | Yamamoto et al. |
| 2006/0128031 A1 | 6/2006 | Robotti et al. |
| 2006/0199193 A1 | 9/2006 | Koo et al. |
| 2006/0269927 A1 | 11/2006 | Lieber |
| 2007/0264634 A1* | 11/2007 | Bock ........................ B82Y 5/00 435/6.11 |
| 2009/0181381 A1 | 7/2009 | Oldham et al. |

FOREIGN PATENT DOCUMENTS

| | | |
|---|---|---|
| WO | 2005/040425 | 5/2005 |
| WO | 2005/075638 | 8/2005 |
| WO | 2006/199193 | 9/2006 |
| WO | 2008/068857 | 1/2009 |

OTHER PUBLICATIONS

International Preliminary Report on Patentability for International Application No. PCT/US2008/068857 dated Jan. 5, 2010.
International Search Report and Written Opinion for International Application No. PCT/US2008/068857 dated Jan. 2, 2009.
Sakata, T. et al., "DNA Sequencing Based on Intrinsic Molecular Charges", *Angewandte Chemie International Edition* 2006, vol. 45, 2006, pp. 2225-2228.

\* cited by examiner

SYSTEMS AND METHODS FOR ELECTRONIC DETECTION WITH NANOFETS

CROSS-REFERENCE TO RELATED APPLICATIONS

This application is a continuation of U.S. application Ser. No. 12/165,379, filed Jun. 30, 2008, which claims priority to U.S. application No. 60/947,247, filed Jun. 29, 2007, which disclosures are herein incorporated by reference in their entirety.

FIELD

This invention relates generally to electronic detection for single molecule sequencing, more particularly to systems and methods for electronic detection with nanoFETs.

DESCRIPTION OF THE RELATED ART

Optical detection platforms such as fluorescence technologies are typically the dominant platform for deoxyribonucleic acid ("DNA") sequencing. The optical detection platforms operate on chemistries based generally on sequence by synthesis, hybridization and ligation. The optical detection platforms typically require fluorescent labeling of the enzyme substrates, such as fluorophore labeled deoxynucleotide-triphosphate ("dNTP"), short probe oligonucleotides, or the enzyme itself. The optimization of the substrate modification is a huge effort in the conventional prior art of optical detection platforms such as zero-mode waveguides, FRET, step-wise, etc. The optimization effort is even greater for single molecule sequencing than for Sanger sequencing.

Recently, it has been shown that it is possible to directly sequence on a small field effect transistor ("FET") (see T. Sakata & Y. Miyahara, Angewandte Chemie 45(14):2225-2228 (2006)). However, the current state of technology has only demonstrated out to ten bases and requires a large number of molecules on the same FET. The method used to carry out the sequencing was an un-terminated stepwise synthesis. Accordingly, there is a need in the art to read additional bases as well as to utilize a single molecule using non-optical FET-based sequencing.

SUMMARY

An embodiment generally relates to a system for electrical charge detection. The system includes a nanoFET device configured with a source, drain, and a gate, where the gate of the nanoFET device is configured to receive a strand of target DNA. The system also includes a solution of charge tags, where the charge tags further include at least one type of nucleotide attached to a charge molecule complex. The system further includes test well configured to situate the nanoFET device in the solution of charge tags and a detector configured to monitor at least one of voltage and current from the nanoFET device. The system yet further includes controller configured to interface with the test well and detector, where the controller is configured to flow in the solution of charge tags into the test well, allow incorporation of the charge tags, cleave the charge tags, and detect at least one of voltage and current by the detector.

Another embodiment pertains to a method of electrical charge detection for single molecule sequencing. The method includes attaching a strand of target DNA to a gate of a nanoFET device and flowing in a solution of charge tags, where a charge tag includes a nucleotide attached to a charge complex. The method also includes incorporating one charge tag into the strand of target DNA and cleaving the charge tags from the strand of target DNA. The method further includes detecting at least one of current and voltage from the nanoFET device.

Yet another embodiment relates to a method of electrical charge detection for single molecule sequencing. The method includes attaching a strand of target DNA to a gate of a nanoFET device and flowing in a solution of charge tags, where a charge tag comprises a nucleotide attached to a charge complex. The method also includes ligation of the charge tags with the strand of target DNA and cleaving the charge tags from the strand of target DNA. The method further includes detecting at least one of current and voltage from the nanoFET device.

BRIEF DESCRIPTION OF THE DRAWINGS

Various features of the embodiments can be more fully appreciated, as the same become better understood with reference to the following detailed description of the embodiments when considered in connection with the accompanying figures, in which.

DETAILED DESCRIPTION OF EMBODIMENTS

Figure 1:
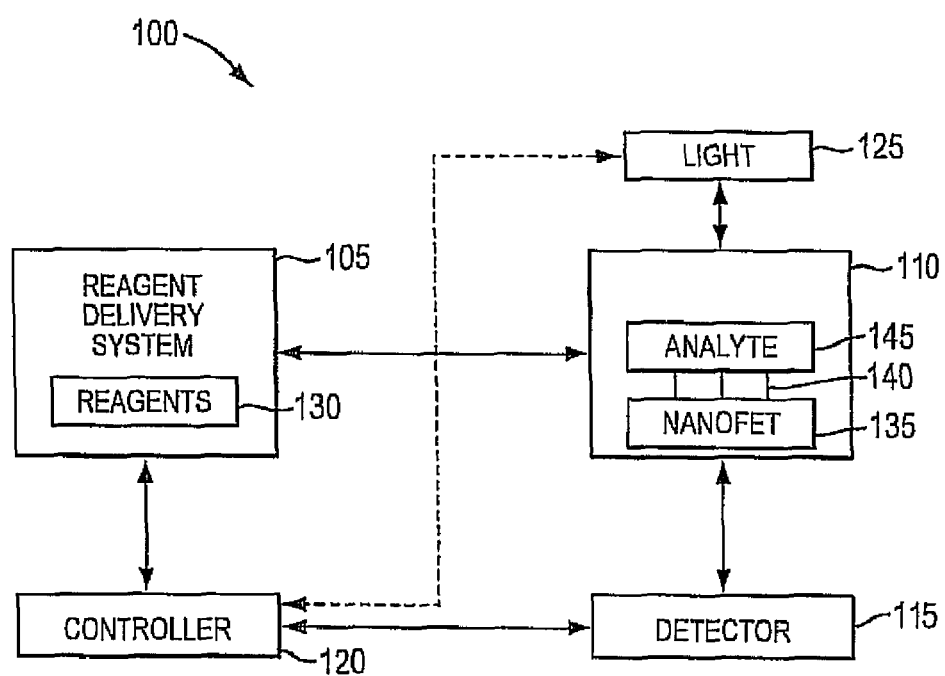
FIG. 1 illustrates an exemplary system in accordance with an embodiment.

For simplicity and illustrative purposes, the principles of the present invention are described by referring mainly to exemplary embodiments thereof. However, one of ordinary skill in the art would readily recognize that the same principles are equally applicable to, and can be implemented in, all types of electronic detection systems and that any such variations do not depart from the true spirit and scope of the present invention. Moreover, in the following detailed description, references are made to the accompanying figures, which illustrate specific embodiments. Electrical, mechanical, logical, and structural changes may be made to the embodiments without departing from the spirit and scope of the present invention. The following detailed description is, therefore, not to be taken in a limiting sense and the scope of the present invention is defined by the appended claims and their equivalents.

Embodiments pertain generally to systems and methods for single molecule sequencing using a nanoFET. More particularly, a nanoFET can be configured to detect charge changes on a strand of nucleic acids, such as DNA (e.g., genomic DNA or cDNA). The nucleic acid strand can also be referred to herein as "polynucleotide template", or alternatively, "target". The polynucleotide template can be attached (ligated) to oligonucleotides (which can be referred to as a "binding primer"), which is then attached to the nanoFET. The binding primer can be a universal primer. The binding primer can also be referred to as a "binding region."

In some embodiments, a reversible attachment can be implemented. Reversible attachment can be implemented in several ways. One technique includes the use of peptide nucleic acids ("PNA") or other similar synthetic oligonucleotides, which have a much higher melting temperature than DNA, and are thus not removed at the temperature used to melt off DNA. A PNA can be attached to the FET, with its complement included as part of the binding region ligated to the polynucleotide template (as a PNA/DNA chimera). The polynucleotide template can then hybridize with the PNA attached to the surface of the FET via the PNA complement within the binding region. The PNA on the FET can be attached using a biotin strepavidin, preferably with the biotin attached to the PNA. The polynucleotide template can then be removed by simply raising the temperature above the PNA melting temperature. Another reversible attachment technique can use a biotin strepavidin bond directly, where the biotin is attached to the universal primer, which is subsequently ligated to the target nucleic acid strand.

An initializing oligonucleotide complementary to the binding region on the polynucleotide template can be introduced to a detection volume associated with the nanoFETs and attached target, under conditions which cause hybridization between the initializing oligonucleotide (also referred to as an "initializing primer" herein) and the binding region. The initializing primer can be a universal primer. A large set of oligonucleotides (also referred to as "probes" herein) with differing charge molecule complexes can be attached thereto, i.e., charge tags, where the charge tag is associated with a base on the polynucleotide template. As the probes are flowed in, they can ligate with the polynucleotide template. This process is described in more detail by U.S. Patent Publication No. 20080003571, relevant portions of which are hereby incorporated by reference.

A blocking group at the end of the probe prevents ligation of more than one probe. The probes can be removed from the detection volume, either by washing or by application of an electric field to pull the probes away from the nanoFET. Probes which have annealed to the target, but have not been ligated, can be removed from the target by the applied electric field, by elevation of the detection volume temperature, or by changing the conditions in the detection volume (pH and ionic concentration). The charge tags can then be cleaved and detection of at least one of current or voltage from the nanoFET is initiated. Most embodiments contemplate using a photolabile linker to attach the charge complex to the probes and light can be used to cleave the charge tag as well as initiate the detection process. In some embodiments, other chemistries, such as chemical cleavage, can be used to separate the charge tags. Removal of the charge tag also removes the blocking group at the end of the oligonucleotide, permitting the ligation of another oligonucleotide. Removal processes are described in more detail by U.S. Patent Publication No. 20080003571, and U.S. Pat. Nos. 5,740,341 and 6,306,597, relevant portions of which are incorporated herein by reference.

If an electric field is used to remove the unligated probes from the detection volume, the field can then be removed or reduced allowing diffusion to bring the primers back into the detection zone, or reversed forcing the probes back into the detection zone, and allowing an additional cycle of ligation and detection. The use of an electric field can enable faster kinetics even with lower average concentrations by increasing the local concentration in the detection zone. Alternatively, if the probes have been washed out of the detection volume, another set of probes with charge tags attached thereto can be added and detected. Accordingly, every fifth base can be determined. After the polynucleotide template is sequenced to the desired length, the entire second strand is melted off.

Subsequently, a second initializing oligonucleotide (second primer) which is one base shorter than the original initializing oligonucleotide (original primer), can be introduced the nanoFET with the attached polynucleotide template. The large set of probes with charge tags attached thereto can then be reintroduced, and the ligation and detection process is repeated until the second strand is completed. The second primer can be a universal primer. The use of the second primer can detect every base offset by one that was previously detected with the first universal primer. The process is then repeated with another intializing oligonucleotide (primer) with one less base until the last base is detected. Each primer can be a universal primer. This process is described in more detail by U.S. Patent Publication No. 20080003571, relevant portions of which are hereby incorporated by reference. This process is also described using fluorescent labels and fluorescent detection for clonal sets of target molecules, as illustrated by published PCT application WO2006084132, which is hereby incorporated in its entirety.

In some embodiments, the detection can be based upon the detection of a single base in the fifth position, and the sequence can be directly determined from a two-base encoding scheme using the primers and the nanoFET. More particularly, a two-base encoded probe can be used to obtain information about the $4^{th}$ and $5^{th}$ bases. The two-base encoding scheme, which is described in published PCT application WO2006084132, interrogates each base twice for errors during sequencing and removes measurement errors. The primer that is ligated and cleaved is described as being five bases in length, but can be other lengths, including from about 2 to about 15 bases, in addition, the detection is described as starting from the fifth position but could start at a different position. An alternative embodiment uses direct interrogation of the probe that is incorporated. A further embodiment uses three or more base encoding.

Another embodiment relates generally to single molecule sequencing with a nanoFET biased with a small electric field. Similar to the previous embodiment, a nucleic acid strand is attached (in some embodiments using reversible attachment) to the gate of the nanoFET via a binding primer. The nanoFET can be positioned within a well with conductive plates. A solution of free charge labeled probes can be then be introduced. A small electric field can be generated between the conductive plates which creates a voltage gradient. Because the charged probes carry a charge, they can be drawn closer to the nucleic acid strand, thus increasing the local concentrations of the charge labeled probes and improving the enzyme kinetics during ligation.

Yet another embodiment pertains to single molecule sequencing with a nanoFET with a voltage gradient to aid the removal of unligated charge labeled probes. More specifically, the target nucleic acid strand can be attached to the gate of the nanoFET via a binding primer in a well with conductive plates. A solution of free charge labeled charged probes can be introduced into the well. As the free charge labeled charged probes hybridize themselves to the target nucleic acid strand by the polymerization process, as known to those skilled in the art, a voltage gradient can be applied to remove any unligated charged probes. As a consequence of this voltage gradient, the charge tags (free charge labeled probes) are pulled up as well as the target nucleic acid strand. The voltage gradient could be applied one or more times. Accordingly, the sensing of the voltage of the nanoFET, and the application of the light used for photocleavage can be timed to occur when voltage gradient is turned on. The effect of the removal of the unligated charge tags can provide a cleaner signal.

In order to speed the process of the extension of primer, the ligating enzyme can be modified such that it has the same sign for its net charge as the sign of the net charge for the charge labeled probes. This can prevent problems resulting from the enzyme migrating in the opposite direction as the probes. The modification can be achieved by exchanging amino acids in non-critical areas of the enzyme to directly modify its net charge, or by attaching a charge tag to the enzyme. The net charge for the enzyme and charge labeled probes can be either positive or negative.

As previously described, a voltage gradient can be used as part of the single molecule sequencing process. As a consequence of this voltage gradient, the charge tags (free charge labeled probes) are pulled up as well as the target nucleic acid strand. Accordingly, the sensing of the voltage of the nanoFET, and the application of the light used for photocleavage can be timed to occur when the voltage gradient is turned on. The effect of the removal of the unligated charge tags can provide a cleaner signal. If the voltage gradient is reversed as previously described to bring the primers into the detection volume, the field can be used to further concentrate the primers into the detection volume, reducing the concentration of primers which would otherwise be needed.

Yet another embodiment pertains to single molecule sequencing with a nanoFET using polymerase. More particularly, polymerase can be attached to the gate of the nanoFET in a test well. A solution of charge labeled probes can be introduced into the test well. The charged complexes can be attached to the respective dNTP with photolabile linkers, which then slow or stop further polymerization additions (thus, functioning as a terminator). Accordingly, this allows the system to be synchronized for improved detection efficiency and improved signal-to-noise detection. This system also allows significant improvement in the ability to distinguish momentary binding events from true incorporation events, as the change in charge changes at a known time (shortly after the light pulse occurs). Alternatively, the label could be attached to the gamma phosphate, permitting "real-time" sequencing. The label could be placed in a number of different locations, including the 2', 3', and 5' positions.

In some embodiments, the well can include conductive plates that can generate a voltage gradient. The voltage gradient can pull away unattached charge tags to improve detection efficiency and signal-to-noise detection.

Yet another embodiment relates generally to polymerase attached to the gate of a nanoFET operating in an alternating current (AC) field to directly read unlabeled nucleic acids. More specifically, an AC field can be generated in a well containing the nanoFET, where the AC field is operating a frequency appropriate with the mass and dipole moment of the unlabeled deoxynucleotide-triphosphates (dNTPs) being used. The nanoFET and amplification system can be configured to measure a good signal-to-noise ratio at speeds greater than the AC field frequency. Alternatively, charge labeled dNTPs could be used, either in a terminating system or a system that does not stop the enzyme activity, particularly where the label can be cleaved or is photolabile. The length of the nucleic acid strand can be minimized in order to maximize the signal-to-noise ratio, although this may be less needed if long nucleic acid strands are used in an entangled polymer with small charge tags in an AC field. If the nucleic acid strand is too long, it may tend to ball up or otherwise interact with the gate of the nanoFET. In some embodiments, the charge tags could also be attached at the gamma phosphate, permitting enzymatic cleavage and the highest speed.

Yet another embodiment relates generally to a charge tag enzyme-linked immunosorbant assay ("ELISA") sandwich assay. More particularly, the nanoFET can be used in an ELISA sandwich assay, where the detection antibody has a charge label. This can be performed with either a single capture antibody or a set of identical antibodies. Other types of sandwich assays can be performed, such as non-antibody. The kinetics of the assay can be directly observed and if a competitive assay is performed, the kinetics associated with each target can be observed.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the mean thermal denaturation temperature ($T_m$) of the formed hybrid. Hybridization methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the hybridization process by Marmur and Lane, Proc. Nati. Acad. Sci. USA 46:453 (1960) and Doty et al., Proc. Natl. Acad. Sci. USA 46:461 (1960), have been followed by the refinement of this process into an essential tool of modem biology.

The term "oligonucleotide" as used herein is understood to mean a molecule comprising two or more deoxyribonucleotides or ribonucleotides, or other synthetic equivalents, preferably at least 5 nucleotides, more preferably at least about 10 to about 15 nucleotides, and more preferably at least about 15 to about 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

The term "label" as used herein is understood to mean any atom or molecule that can be used to provide a detectable (preferably quantifiable) signal, and that can be attached to a nucleic acid or protein. Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

As used herein, the term "charge tag" is understood to mean a modular chemical complex that is attached to or to be attached to another molecule, wherein the charge tag has a net charge that differs from the net charge of the other molecule. For example, charge tags may be attached to nucleic acid molecules. Charge tags can be attached to the phosphate group or a nucleotide at the alpha, beta, or gamma positions of the triphosphate group, or can be attached to the fourth position of a four phosphate group, etc. Additionally, the charge tag can be attached to the 2', 3', 4' positions or some combination on the sugar of a nucleotide, or can be attached to the base of the nucleotide. Charge tags contain any number of desired components including, but not limited to, dyes, linker groups, nucleotides, phosphoramidites, phosphonates, phosphate groups, amine groups, fluorescent quencher groups and the like.

As used herein, the term "macromolecule or assemblies thereof" is understood to mean a molecule having high relative molecular mass (e.g., molecular mass greater than a few thousand daltons) and aggregates of such molecules. Non-limiting examples of macromolecules include nucleic acids, proteins (e.g., enzymes, antibodies, and the like), polysaccharides (e.g., carbohydrates), and lipids. Non-limiting examples of assemblies of macromolecules include subcellular components, such as cell membranes and organelles. In an embodiment, the macromolecule can be a strand of nucleic acids, such as target DNA or target RNA. In another embodiment, the macromolecule can be a polymerase. In a further embodiment, the macromolecule can be an antibody.

FIG. 1 shows an exemplary detection system 100 in accordance with an embodiment. It should be readily apparent to those of ordinary skill in the art that the detection system 100 depicted in FIG. 1 represents a generalized schematic illustration and that other components may be added or existing components may be removed or modified.

As shown in FIG. 1, the detection system 100 includes a reagent delivery system 105, a nanoFET assembly 110, a detector 115, a controller 120 and/or a light source 125. The reagent delivery system 105 can transfer one or more reagents 130 for nucleic acid modification, and particularly fluid reagents, to and/or from the nanoFET assembly. The reagent delivery system 105 can be a flow-based system including a pump(s), a valve(s), one or more reservoirs, a channel(s) in which the nanoFET assembly 110 is disposed, and/or the like.

The nanoFET assembly 110 can provide a site for nucleic acid modification. More particularly, the nanoFET assembly 110 can include a nanoFET 135 and one or more nucleic acids 140 (such as binding primer) coupled to the nanoFET 135. The nucleic acids 140 can then be coupled to an analyte 145 (such as the target DNA). Alternatively, the target DNA can be ligated to the binding primer prior to introduction to the nanoFET for attachment. The nanoFET 135 is generally known to those skilled in the art. The nanoFET 135, like conventional FET, include a source, a drain and a gate. The nanoFET assembly can contain a single nanoFET, or a plurality of nanoFETs, permitting parallel sequencing of multiple DNA targets. The nanoFET can be a gold nanowire FET as described in U.S. Patent Publication No. 20060269927, the description of which is hereby incorporated by reference in its entirety. Alternatively, the nanoFET can be a carbon nanotube FET, or a silicon nanoFET.

The detector 115 can be configured to measure a parameter such as an electrical characteristic (e.g., voltage, current, etc.) of the nanoFET assembly 110, more specifically, the nanoFET 135. Accordingly, the detector 115 can be electrically coupled to the nanoFET 135 (not shown) to measure electrical characteristics thereof, which can be positioned in a detection volume (or test well).

The controller 120 can be configured to control and manage various aspects of the operation of the detection system 100. For example, the controller 120 can be configured to flow in initializing primers, charge labeled oligonucleotides (probes), charge labeled nucleotides, ligase, polymerase, or wash solutions, from the reagent delivery system 105 to the nanoFET assembly 110. As another example, the controller 120 can be coupled to the detector 115 to determine when the detector 115 measures the electrical characteristics of the analyte 145. The controller 120 can be implemented with internal hardware such as a Field Programmable Gate Array (FPGA), an internal microcontroller, a server, a workstation, a personal computer or other similar computing platform equipped with appropriate interfaces for the reagent delivery system 105, detector 115 and the light 125.

The controller 120 can also be configured to be coupled with a light source 125. The light source 125 can be configured to be used to photocleave charged oligonucleotides (or charge tags) from the analyte 145, typically using a pulse or burst of light. The pulse or burst of light from light source 125 can also mark the initiation of the detection process. As most photocleavable linkers respond to UV, the light source 125 is preferably a UV laser or UV LED. The light from fight source 125 can be focused so that it interacts with probes which are ligated to the target, and not with those probes which have not been ligated. For example, light from light source 125 can be localized to the detection area by Total Internal Reflection Fluorescent Microscopy (TIRFM). The light source 125 can be a flood source, so that a large number, or all of the nanoFETs, are illuminated at once. Alternatively, the light source 125 can be configured as a line source or a point source, which can then be scanned across an array of nanoFETs. Using a flood source allows all of the reactions to proceed synchronously, while using a line or point source permits use of a detector for more than one nanoFET, whereby for example, an analog multiplexer can be used to allow a detector to process the signal from more than one nanoFET.

Figure 2:
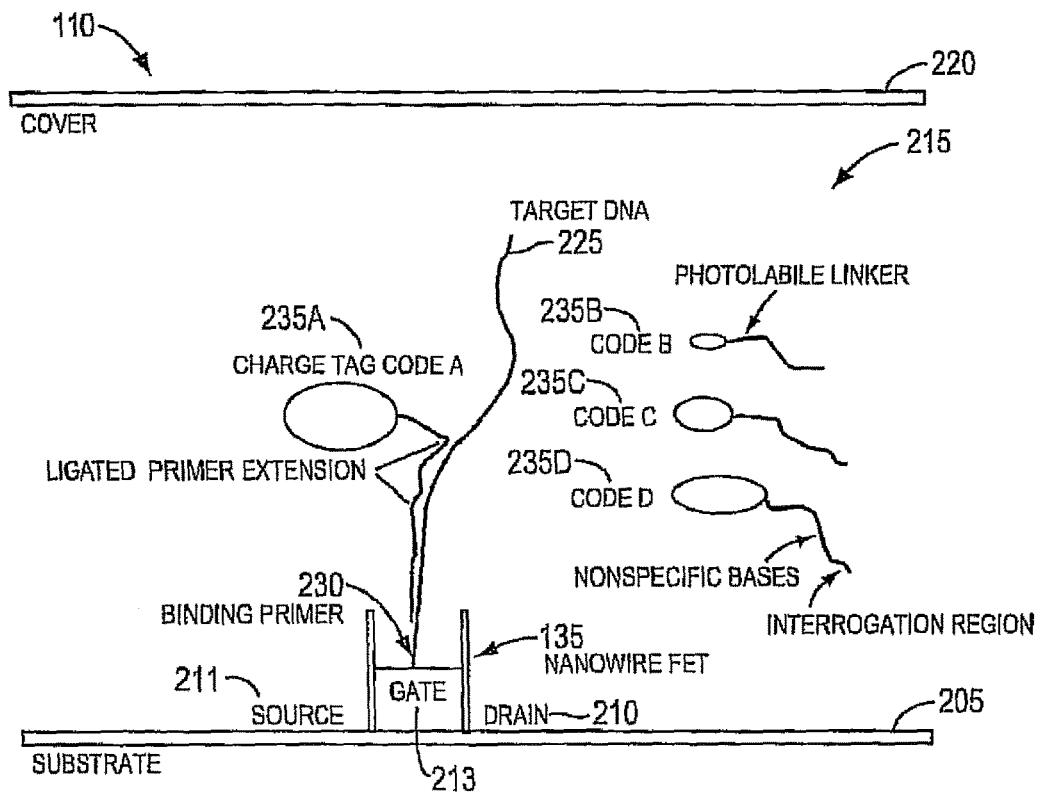
FIG. 2 depicts a more detailed view of the nanoFET assembly of the system shown in FIG. 1 in accordance with another embodiment.

FIG. 2 shows a more detailed view of the nanoFET assembly 110 in accordance with another embodiment. It should be readily apparent to those of ordinary skill in the art that the nanoFET assembly 110 depicted in FIG. 2 represents a generalized schematic illustration and that other components may be added or existing components may be removed or modified.

As shown in FIG. 2, the nanoFET assembly 110 can include a substrate 205 where a nanoFET 135 can be attached. The substrate 205 can form a structural member of the test well 215. A cover 220 can be another structural member of the test well 215 as well as side walls (not shown). Further not depicted for the sidewalls are valves opening for solutions to flow in and out of the test well 215.

Figure 2A:
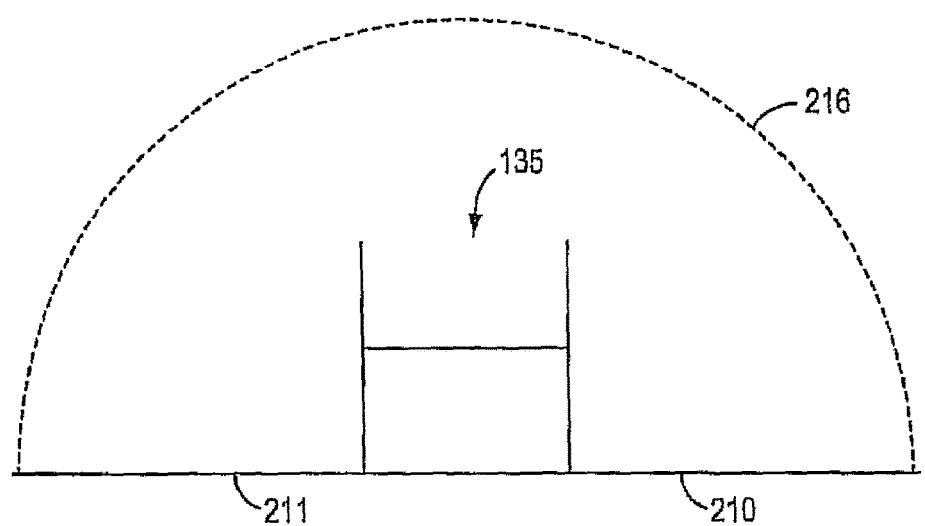
FIG. 2A depicts a view of a detection volume associated with the nanoFET in accordance with yet another embodiment.

The nanoFET 135 can be configured to be an electrical sensor for the selected target DNA. The nanoFET 135 can be implemented using nanotechnologies known to those skilled in the art, such as U.S. Patent Publication 200610154400 and/or U.S. Patent Publication 2006/0154400, the descriptions of which are herein incorporated by reference in their entirety. The nanoFET 135 can include a source 211, a drain 210 and a gate 213. The nanoFET 135 can generate a detection volume as shown in FIG. 2A. In FIG. 2A, the nanoFET 135 can generate a detection volume 216. The nanoFET 135 can detect charges within the detection volume 216. The volume of the detection volume 216 can be dependent on the type of solutions that are washed in as well as the type of charged labeled oligos or nucleotides being used.

A target DNA 225 can be attached to the gate 213 via a binding primer 230. The binding primer 230 attachment to the gate 213 can be a reversible attachment in some embodiments, so that the target DNA 225 and binding primer 230 can be removed and replaced with another target DNA 225 and binding primer 230. The target DNA 225 and binding primer 230 can be removed using an electric field, temperature, or change in the conditions of the detection volume around the nanoFET (such as pH, ionic concentration, or by addition of silver or other cleavage agents). The nanoFET 135 and the target DNA 225 can be immersed in a solution of charge labeled probes, where the solution or mixture can be flowed in from the reagent delivery system 105. The solution can contain four different sets of probes with charge labels (i.e., charge tags) 235A-D: charge tag 235A can represent a first code (labeled as code A); charge tag 235B can represent a second code (labeled as code B); charge tag 235C can represent a third code (labeled as code C); and charge tag 235D can represent a fourth code (labeled as code D).

The charge labeled probes 235A-D can then be ligated to the target DNA 225. Each of the ligated charge labeled probes indicates a position on the target DNA 225. However, when the solution of initializing primer with charge labeled probes is flowed in, the probe has five bases on the 3' side of the cleavable linker, plus the three universal bases on the 5' side of the cleavable linker, for a total of eight (in other embodiments, 3, 4, 6, or 7 bases can be used on the 3' side of the cleavable linker with varying numbers of universal bases on the 5' side of the cleavable linker). The optimum number of bases will primarily depend on the ligase enzyme used.

After ligation, the ligated probe can then be cleaved, since each charge tag 235A-D can include a photolabile linker to allow the charge tag to be cleaved by light or other energy that creates an evanescent wave. Light can be localized to the cleavage area by TIRFM; by a plasmonic structure, such as that described in U.S. Patent Publication Nos. 20080066549 and 20080105831, relevant portions of which are hereby incorporated by reference; by zero-mode clad waveguides (ZMWG), such as that as described in U.S. Pat. No. 6,917,726, relevant portions of which are hereby incorporated by reference; and combinations thereof. Other embodiments can use chemistry or enzymes to cleave the charge tags. The detector 115 can then be activated to detect the change in charge on the target DNA, which should occur during or shortly after the light pulse. The detection process can be timed with emitting light from the light source 125. Additional ligation can then occur, followed by additional cleavage and detection. Subsequently, the second strand of the target DNA 225 is melted off. The existing solution can be flowed out and a new solution can be introduced to repeat the process, where the solution comprises initializing primers that are one base shorter than the initializing primers in the previous solution. The process is repeated until all the bases are determined.

Figure 3:
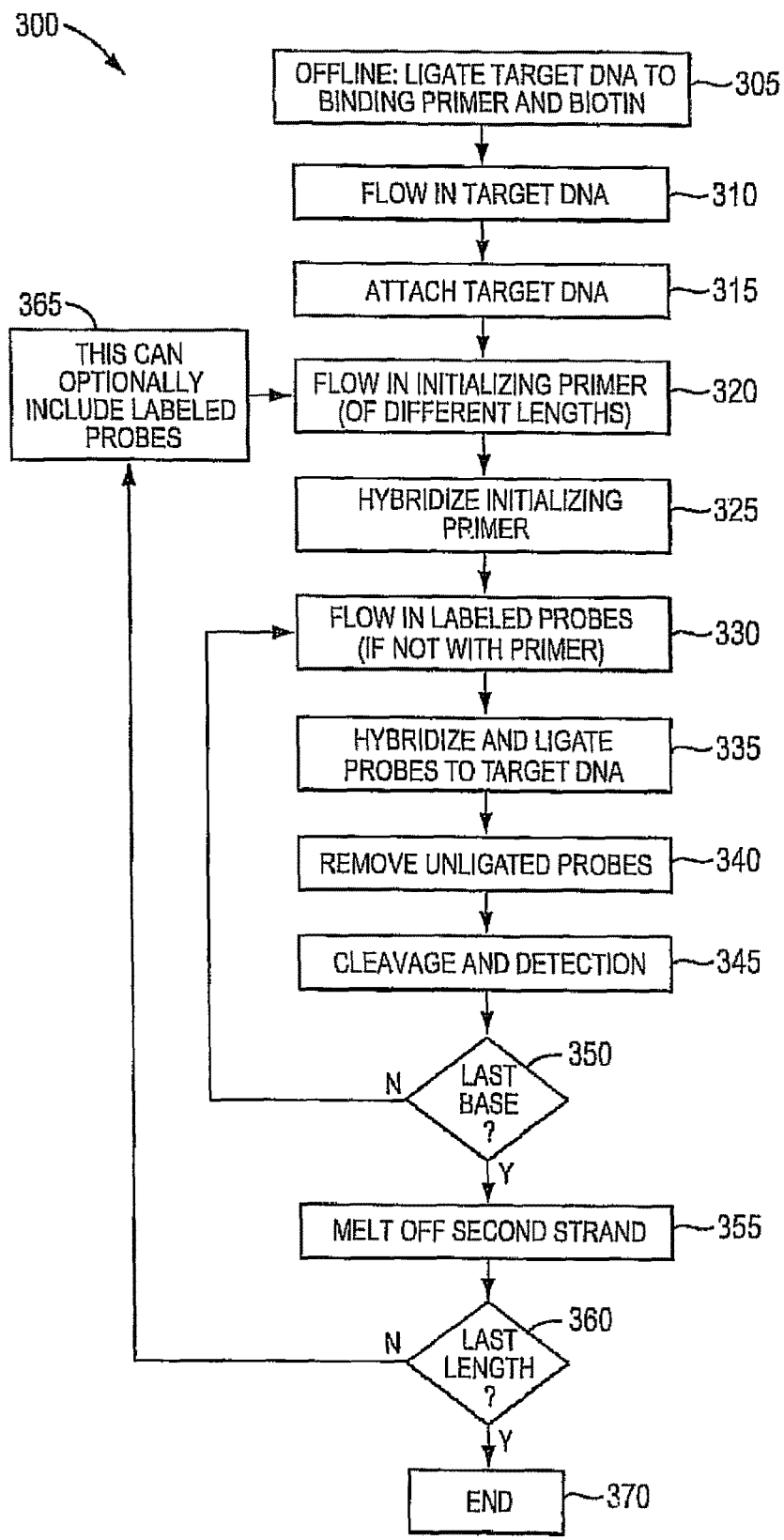
FIG. 3 illustrates an exemplary flow diagram executed by the system shown in FIG. 1 in accordance with yet another embodiment.

FIG. 3 depicts an exemplary flow diagram 300 implemented by the detection system 100 (shown in FIG. 1) in accordance with yet another embodiment. It should be readily apparent to those of ordinary skill in the art that the flow diagram 300 depicted in FIG. 3 represents a generalized schematic illustration and that other steps may be added or existing steps may be removed or modified.

As shown in FIG. 3, prior to placing the target DNA 225 in the nanoFET assembly 110, a user can ligate the target DNA 225 to a binding primer and to biotin, in step 305. This step can be done prior to the beginning of the detection and sequencing. The user can then attach the target DNA 225 in the nanoFET assembly 110.

In step 310, the user can place the target DNA 225 in a solution and flow in the target DNA into the test well 215 of the nanoFET assembly 110. The user can then wait for the free end of the target DNA to attach to the gate 213 based on the chemistry between the material of the gate and the binding primer, in step 315. In some embodiments, the attachment can be a reversible attachment.

In step 320, the controller 120 can be configured to flow in the initializing primer with different lengths. Optionally, charge labeled probes can be flowed in. The controller 120 can be configured to wait for the initializing primer (and probes) to hybridize with the target DNA 225, in step 325.

In step 330, the controller 120 can flow in charge labeled probes if they were not introduced in the previous step. In step 335, the controller 120 can be configured to wait for the charge labeled probes to hybridize and ligate with the target DNA 225.

In step 340, the controller 120 can be configured to flow out any unligated probes. More particularly, the removal of unligated probes reduces the background noise and thus provides for a stronger signal-to-noise ratio.

In step 345, the initiation of light from light source 125 can coincide with the beginning of the detection process by the detector 115 as well as cleave any attached charge tags. The detection is done as part of the cleavage process as it is not possible to determine which signal during the hybridization and ligation process results from the probe that is ligated onto the extended initializing primer. The detector 115 can be configured to sense the current and/or voltage on the gate 213 of the nanoFET 135. The recorded data can then be stored in the controller 120 for later processing. Unlike the existing art, it is relative unimportant whether the ligation efficiency is high. If ligation does not occur in one cycle, it can be repeated without reducing the quality of the data. This permits optimizing for specificity of the enzyme, rather than for both specificity and efficiency. The controller 120 can be configured to determine whether this is the last ligation cycle for this primer. This can be a preset number, or can be determined as a result of analysis of the data quality, or both.

In step 350, the controller 120 can determine whether the last base has been detected. More specifically, the solution of initializing primers and charge tags can be configured to detect every $n^{th}$ base on a DNA strand. Another solution of initializing primers, which are one base shorter than the previous initializing primers, are then used to detect the base position one below the prior position. For a complete sequence, n cycles have to be performed for the number of bases.

If the controller 120 determines that the last base has not been detected, the controller 120 can return to the processing associated with step 330. Otherwise, the controller 120 can then melt off the second strand of DNA from the target DNA 225, in step 355.

In step 360, the controller 120 can be configured to determine if the last length has been detected. More specifically, universal primer was flowed in with a number, m, of different lengths in step 320. Accordingly, the controller 120 can be configured to sequence m times for the number of different lengths.

If the controller 120 determines that the last length has not been detected, the controller 120 can optionally add labeled probes to the solution in step 365. Subsequently, the controller 120 executes the processing of step 320.

Figure 4:
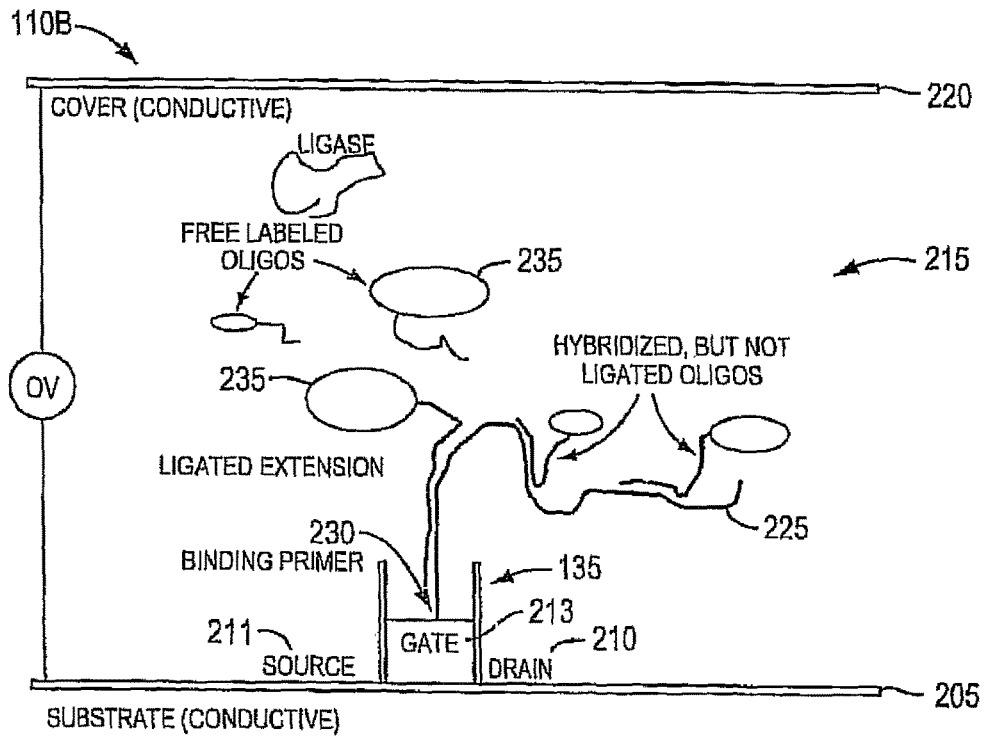
FIG. 4 shows a nanoFET assembly without a voltage gradient in accordance with yet another embodiment.

FIG. 4 shows a more detailed view of a nanoFET assembly 110B with an electric field in accordance with another embodiment. It should be readily apparent to those of ordinary skill in the art that the nanoFET assembly 110B depicted in FIG. 4 represents a generalized schematic illustration and that other components may be added or existing components may be removed or modified. Moreover, FIG. 4 and FIG. 2 share some common features. Accordingly, the description of the common features in FIG. 4 is being omitted and that the description of these features with respect to FIG. 2 is being relied upon to provide adequate description of the common features.

As shown in FIG. 4, the nanoFET assembly 110B includes the nanoFET 135 in a solution of charge tags 235. The charge tags 235 can include free labeled probes which have not hybridized. The nanoFET assembly 110 can also include charge electrodes (not shown) as part of the substrate 205 and cover 220, respectively. The charge electrodes provide a small electric field, in some embodiments in the range of about 0.1 V/cm to about 100 V/cm that drive the charge tags 235 down to the nanoFET 135. As a result, the concentration of charge tags 235 can be increased, thus increasing the kinetics of the process. In addition, an AC field may be superimposed on the DC field to provide better kinetics and specificity. The DC component brings the probes into the detection region at a high concentration, while the AC field is used to remove mishybridized probes, providing room for the correct probes to hybridize. The magnitude of the AC field must be matched to the strength of the DC field, such that there are intervals where there is comparatively little field preventing hybridization, and intervals where the field strength is strong enough to remove mishybridized probes, but not strong enough to remove properly hybridized probes, or properly hybridized and ligated probes. The frequency of the AC field must be slow enough to permit probes to be pulled away from their mishybridized positions. This combination of fields can be used with any hybridization process. The process of detection for this embodiment of the nanoFET assembly 110B generally follows the flow diagram 300.

Figure 5:
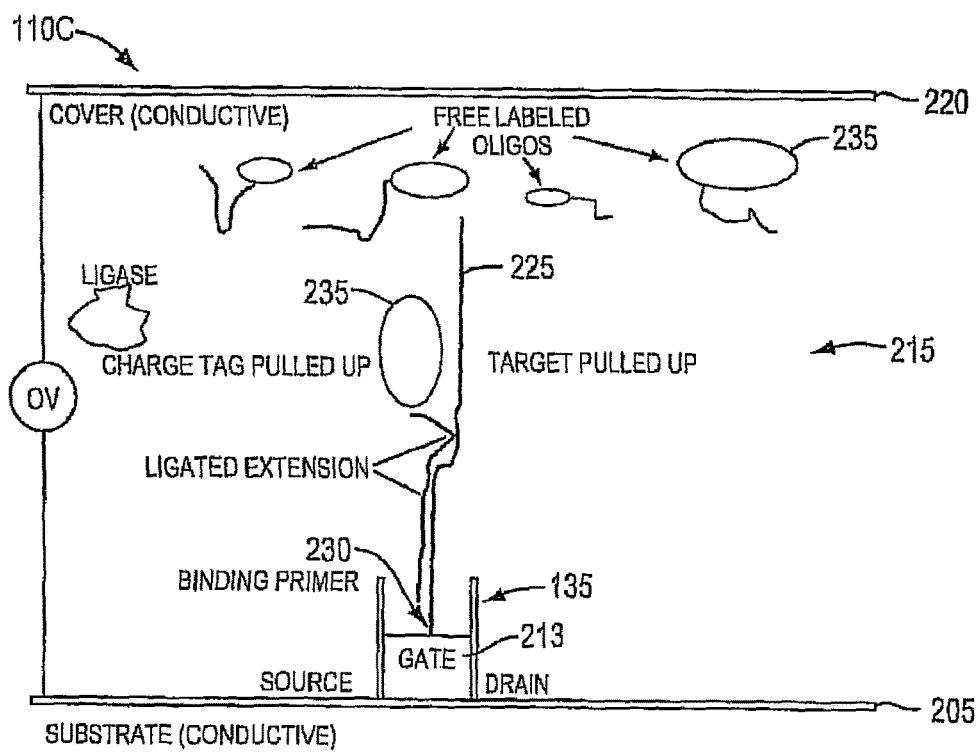
FIG. 5 depicts a nanoFET assembly with a voltage gradient to remove unligated oligos in accordance with yet another embodiment.

FIG. 5 shows a more detailed view of a nanoFET assembly 110C with an electric field in accordance with the embodiment of FIG. 4 during the detection phase. As shown in FIG. 5, the nanoFET assembly 110C includes a nanoFET 135 in a test well 215. The test well 215 can further comprise the substrate 205 and cover 220 with charge plates (not shown) incorporated therein. The controller 120 can be configured to apply a bias substantially in the range between about 0.1 V/cm to about 100 V/cm within the test well 215 between the substrate 205 and the cover 220. As a result, the bias voltage can put the charge labeled probes 235 in a known state as well as removing hybridized but unligated charge labeled probes, or unhybridized (free) charge labeled probes and the target DNA 235. One advantage of this embodiment of the nanoFET assembly 110C is that it requires less reagent since the charge labeled probes can be directed in and out of the detection region and away from the nanoFET 135 and the reagent would not have to be flowed in and out. Another advantage can be that the nanoFET assembly 110C performs faster because washing of the charge tags is not required.

Figure 6:
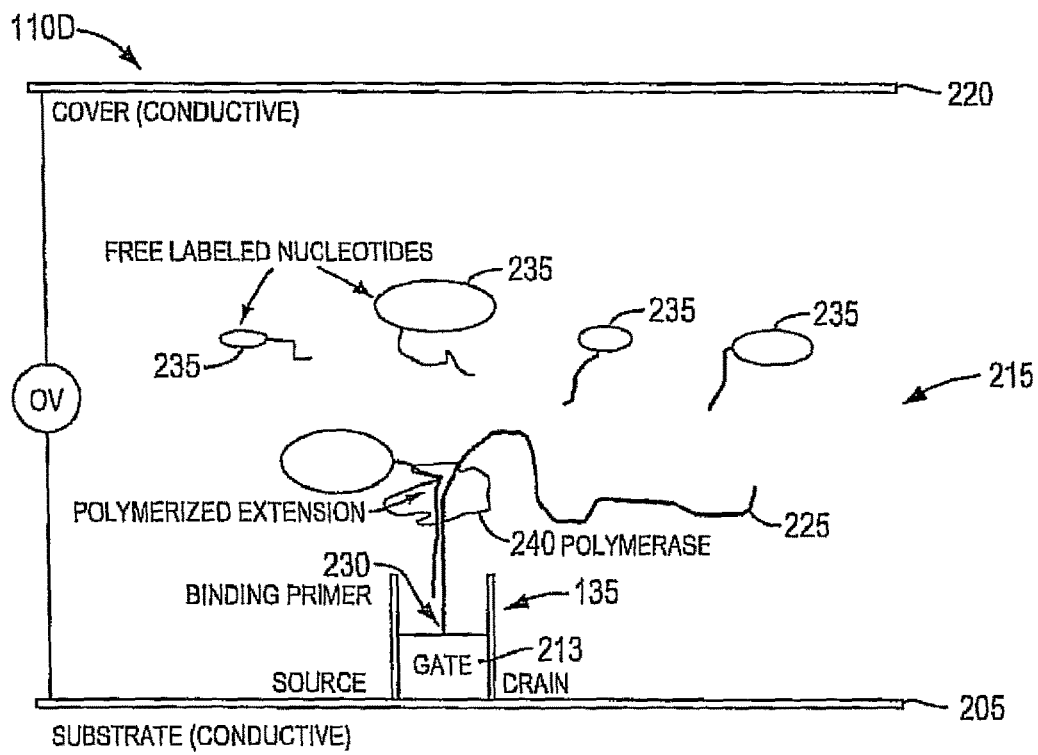
FIG. 6 illustrates a nanoFET assembly with polymerase in accordance with yet another embodiment.

FIG. 6 shows a more detailed view of a nanoFET assembly 110D with a polymerase attachment of the target DNA in accordance with yet another embodiment. It should be readily apparent to those of ordinary skill in the art that the nanoFET assembly 110D depicted in FIG. 6 represents a generalized schematic illustration and that other components may be added or existing components may be removed or modified. Moreover, FIG. 6 and FIG. 2 share some common features. Accordingly, the description of the common features in FIG. 6 is being omitted and that the description of these features with respect to FIG. 2 is being relied upon to provide adequate description of the common features.

As shown in FIG. 6, the nanoFET assembly 110D include a nanoFET 135 in a test well 215. A solution of charge tags 235 and polymerase 240, where the charge tags can be charge labeled deoxynucleotide-triphosphates (dNTPs), tetraphosphates or more, can be placed into the test well 215. The solution of charge tags 235 can contain four types of charges that correspond to the complementary bases of DNA. The target DNA 225 is attached to the gate 213 of the nanoFET 135. Polymerases are enzymes that catalyze the synthesis of nucleic acids on preexisting nucleic acid templates, assembling RNA from ribonucleotides or DNA from deoxyribonucleotides.

As the mixture (or solution) of charge tags 235 is introduced into the test well 215, one of the four types of charge tags can be polymerized onto the target DNA 225. The charge tag can be attached to the sugar or the base of the nucleotide with a cleavage linker, such as a photolabile linker. Other embodiments contemplate using chemical cleavage linkers.

As the appropriate charge tag 235 is bound and incorporated into the polymerized binding primer 230, the charge of the selected charge tag 235 can be blocked by the cleavable linker. The light source 125 can be initiated and detection of current and/or voltage of the nanoFET 135 can be performed by the detector 115. When the cleavable linker is cleaved off, the next charge tag 235 complementary to the next charge labeled base of the target DNA 225 can float in, bind with the target DNA 225, be incorporated by the polymerase, and be detected. Unlike the ligase approach, which detects every fifth base, this detection process detects each base in sequence.

In another embodiment, the charge tags 235 can be dNTPs with the appropriate charge tag attached to the phosphate group without a cleavable linker. The charge tag 235 can then be cleaved by the polymerase 240 at the time of incorporation. Detection would occur at hybridization and incorporation phase, and then the charge tags are floated off.

This process has the possibility of false readings. More particularly, using charge tags attached to the phosphate group of the dNTP can be dependent on the enzymes. Enzymes can go forward as well as go backward. To the extent that an enzyme backs up, an additional base can be reincorporated into the vacancy created by the exonuclease activity of the enzyme. This looks like a natural incorporation, which provides the false reading. Thus, an enzyme that has no exonuclease activity is desirable. In addition, bases can bind but not be incorporated into the extended primer. This can also look like the same as an incorporation event. A further option is thus to use the charge labels as reversible terminators, which can then be removed synchronously, providing greatest assurance that a measured signal is actually an incorporation event. A similar configuration is described by PCT publications WO9627025 and WO05040425, the descriptions of which are both hereby incorporated in their entirety.

Figure 7:
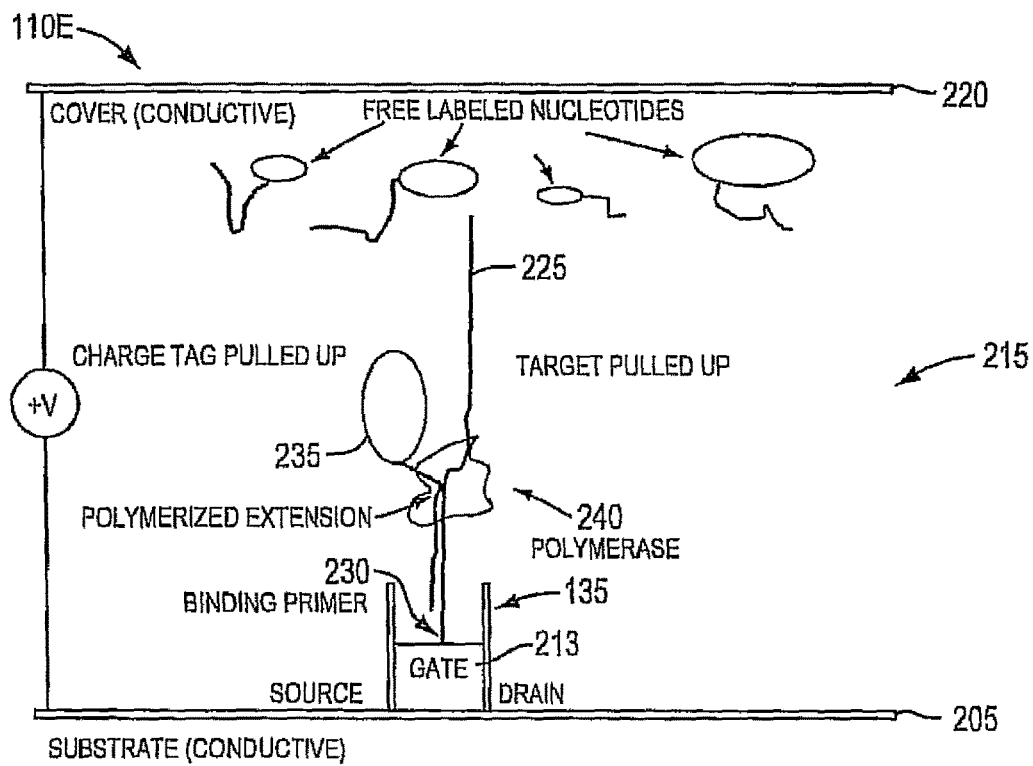
FIG. 7 shows a nanoFET assembly with polymerase with a voltage gradient in accordance with yet another embodiment.

FIG. 7 shows an optional part of the embodiment described as part of FIG. 6, where an electric field is applied to bring the DNA 225, polymerase 240, and newly incorporated charge labeled nucleotide into a known position to provide better determination as to which charge label was incorporated. The nanoFET signal is a function of both the amount of charge, and the distance the charge is away from the gate of the nanoFET, so controlling the distance improves the ability to determine the quantity of charge.

It should be readily apparent to those of ordinary skill in the art that the nanoFET assembly 110E depicted in FIG. 7 represents a generalized schematic illustration and that other components may be added or existing components may be removed or modified. Moreover, FIG. 7 and FIG. 6 share some common features. Accordingly, the description of the common features in FIG. 7 is being omitted and that the description of these features with respect to FIG. 6 is being relied upon to provide adequate description of the common features.

As shown in FIG. 7, the nanoFET assembly 110E can include a nanoFET 135 in a test well 215. The test well 215 can contain a solution of charged dNTPs, where each base of the dNTP can be assigned a charge value. The charge can be attached to the sugar or base to the dNTP by a cleavable linker, such as a photolabile linker, chemical cleavable linker, or other type linker. The combination of charge and dNTP can comprise the charge tags 235.

The test well 215 can further comprise the substrate 205 and cover 220 with charge plates (not shown) incorporated therein. The controller 120 can be configured to apply a bias voltage of less than about 0.1 V/cm to about 100 V/cm to the charge plates to generate an electric field within the test well 215 between the substrate 205 and the cover 220. As a result, the charge labeled probes (charge tags) 235 are pulled up along with target DNA 225. The electric field can put the charge tags 235 in a known state as well as pull up any attached charge tags and the target DNA 225. One advantage of this embodiment of the nanoFET assembly 110E is that it requires less reagent since the charge tags can be directed in and out of the nanoFET 135. Another advantage can be is that nanoFET assembly 110E performs faster since washing of the charge tags is not required.

Although FIG. 7 depicts the nanoFET 135 of the nanoFET assembly 110E in a vertical orientation, the nanoFET 135 can be on a side wall of the test well 215 and aligned with a channel that extends from the gate 213 of the nanoFET 135 with the cover 220 or substrate 205. This particular configuration can increase the concentration of the charge tags 235 (surrounding the nanoFET 135) and in some instances pull the charge tags to the nanoFET 135. In addition, although the figure shows the one electrode below and adjacent to the FET and the second on the top cover, the second could be on a side wall, or on the same surface as the FET but at a distance from the FET.

Figure 8:
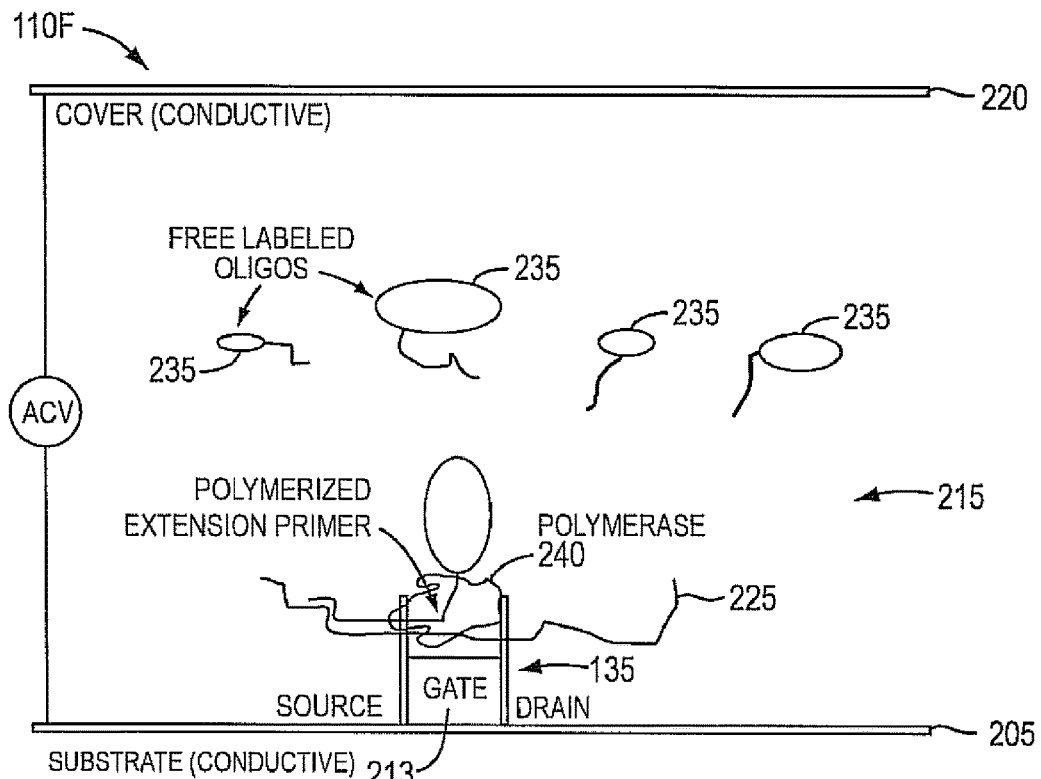
FIG. 8 depicts a nanoFET assembly with polymerase attachment with an AC field in accordance with yet another embodiment.

FIG. 8 shows a more detailed view of a nanoFET assembly 110F with a polymerase attachmed to the nanoFET in accordance with yet another embodiment. It should be readily apparent to those of ordinary skill in the art that the nanoFET assembly 110F depicted in FIG. 8 represents a generalized schematic illustration and that other components may be added or existing components may be removed or modified. Moreover, FIG. 8 and FIG. 6 share some common features. Accordingly, the description of the common features in FIG. 8 is being omitted and that the description of these features with respect to FIG. 6 is being relied upon to provide adequate description of the common features.

As shown in FIG. 8, the nanoFET assembly 110F include a nanoFET 135 in a test well 215. A solution of charge labeled nucleotides (charge tags 235), where the charge tags 235 are free labeled dNTPs with a charge attached thereto, can be placed into the test well 215. The test well 215 can further comprise the substrate 205 and cover 220 with charge plates (not shown) incorporated therein. Similar to the embodiment shown in FIG. 6, the target DNA is held in close proximity to the gate 213 of the nanoFET 135. One main difference between the embodiment shown in FIG. 8 and that of the embodiment shown in FIG. 6 is that instead of attaching the target DNA to the nanoFET, the polymerase is attached to the nanoFET. This insures that the distance from the charge labeled nucleotide to the gate remains the same as additional bases are added, while in the case of the embodiment of FIG. 6, the distance grows with each incorporation of a base. Thus, the embodiment of FIG. 8 is likely to enable longer reads, and also permits the nanoFET to read multiple target DNAs. The embodiment of FIG. 6 has the advantage that the target DNA is fixed, permitting melting off the second strand and resequencing the target. The second difference is that an AC field is shown in FIG. 8. The AC field is used to assist in the measurement of the charge labels. The frequency of the AC field can be varied, and tuned to match the resonance of the dipole of the charge tag. The output of the nanoFET 135 and the detector 115 can then be filtered to look for the resonance, as can be done with a lock in amplifier such as a Stanford Research Systems SR830. The frequency can be varied to match each of the four different charge tags. Alternatively, Fourier transforms can be applied to data resulting from pulsed square waves, or other similar wave functions, which can then be used to determine which of the four tags, if any, is present.

This configuration of the nanoFET assembly 110F has the advantage is that the charge is close and in the same place relative to the gate 213 of the nanoFET 135.

Moreover, the charge tags can be attached not to the gamma phosphate area but to a sugar or base with a photolabile linker, which can be subsequently cleaved, permitting synchronous, and thus more assured, detection. Accordingly, the charge tags can be incorporated, the area surrounding the nanoFET 135 can be cleared of unattached charge tags, and then a reading by the detector 115 using charge detection methods can be performed. The charge of the charge tags 235 can then be cleaved off thus preparing the target DNA 225 for the next incorporation. Because the charge does not move away from the gate, high processivity enzymes such a phi-29 polymerase can be used to sequence long sequences of DNA, which can improve the kinetics of the reaction.

Figure 9:
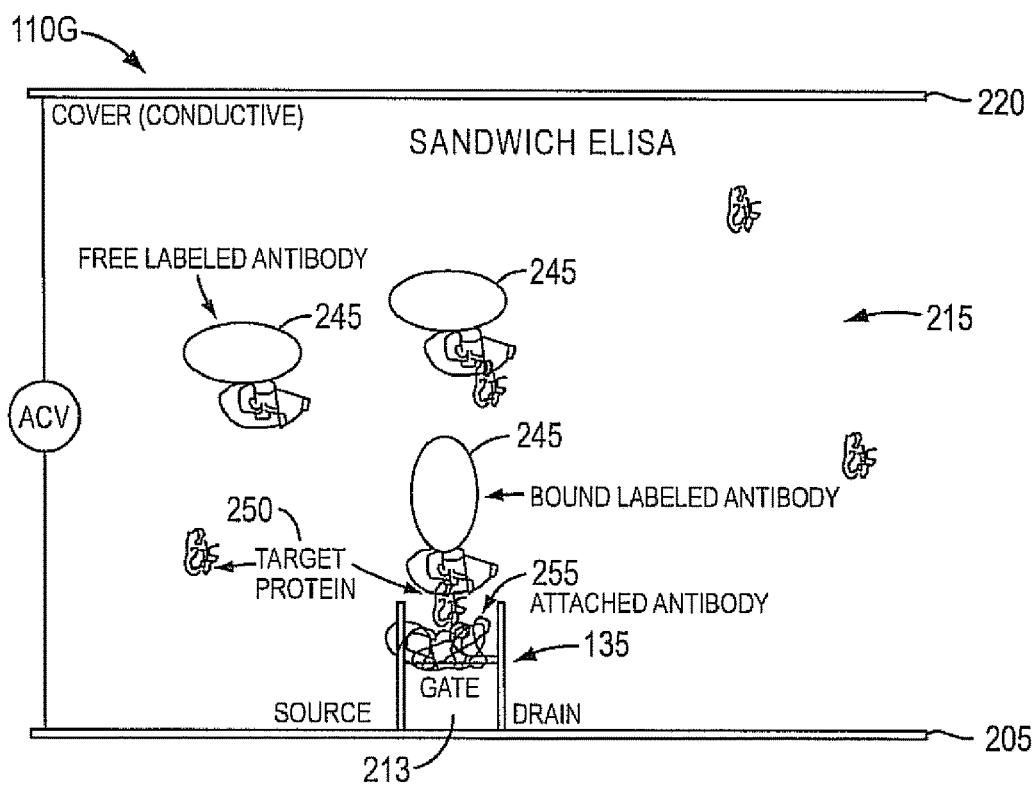
FIG. 9 illustrates a nanoFET assembly for sandwich ELISA in accordance with yet another embodiment.

FIG. 9 shows a more detailed view of a nanoFET assembly 110G with a sandwich ELISA assay in accordance with yet another embodiment. It should be readily apparent to those of ordinary skill in the art that the nanoFET assembly 110G depicted in FIG. 9 represents a generalized schematic illustration and that other components may be added or existing components may be removed or modified.

As shown in FIG. 9, the nanoFET assembly 110G can comprise a nanoFET 135 in a test well 215. The test well 215 can contain a solution of charge labeled antibodies 245, where each antibody has a charge attached thereto or has a charge that is intrinsically associated therewith. An antibody 255 can be attached to the gate 213 of the nanoFET 135. A target protein 250 can then be attached to the antibody 255, and further attached to charge labeled antibody 245.

The test well 215 can further comprise the substrate 205 and cover 220 with charge electrodes (not shown) incorporated therein. The controller 120 can be configured to apply a DC and or AC voltage to the charge electrodes to a voltage substantially between about 0.1 V/cm to about 100 V/cm to generate an electric field. The electric field can then push the charge tags 245 and target protein 250 toward the attached antibody, which will improve the kinetics of the reactions.

This embodiment can be used to detect uncharged proteins. More specifically, the unlabeled protein (target protein 250) can be detected when it is bound to the charge labeled antibody 245 and bound to a second antibody, which is attached to the gate 213 of the nanoFET 135. This arrangement can also be used to monitor kinetics because the use of the charged moiety increases the robustness of the overall system. That is, additional charge can be used to further distinguish certain antibodies or proteins. Other embodiments can substitute proteins instead of antibodies. This approach further provides the option of greater specificity in detection when the attached antibody 255 and the charge labeled antibody 245 are different antibodies. An alternative embodiment monitors several antibody binding reactions simultaneously, which can be accomplished by varying the charge of the different antibodies such that the binding of each antibody can be distinguished from the others. Non-limiting examples of several antibodies include at least three antibodies, for example about three to about ten different antibodies. Greater specificity can be achieved when each antibody comprises a distinct charge, therefore permitting detection of as many antibodies as there are distinct charges.

Although the described embodiments feature a single nanoFET, it should be readily obvious to one of ordinary skill in the art that an array of nanoFETs could be implemented in the various nanoFET assemblies. Similarly, an array of channels can also be used to increase the throughput.

A nanoFET array could be implemented utilizing standard semiconductor processing techniques or could be created using direct electron beam lithography, or using nanoimprinting techniques. The nanoFET could be a carbon nanotube FET gold nanowire FET or a microwave FET.

A nanoFET array could utilize individual amplifier circuits (or pre-amplifier circuits) or could use analog multiplexers with or without individual pre-amplifiers.

Data can be collected using additional reads before and/or after a cleavage step. Data could also be collected by the controller in real time so that binding events and cleavage could be observed, accounting for drift and low bandwidth noise, as two events of opposite sign will occur for any true incorporation.

It is likely that observing immediately before and after cleavage will give the best signal-to-noise detection, as the time associated with the cleavage event will be fairly short. Accordingly, errors due to baseline shift or low bandwidth noise can be minimized. If a point scanner is used with a photolabile linker, a multiplexer can be synchronized with the movement of the scanner. Similarly, if a line scanner is used, a set of multiplexers can track the progression of the line scan.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method may be performed in a different order than illustrated or simultaneously. Those skilled in the art will recognize that these and other variations are possible within the spirit and scope as defined in the following claims and their equivalents.

What is claimed is:

1. A method of detecting a target protein, the method comprising:
    attaching a first antibody to a surface of a device, the device having at least one nanoFET disposed in a well, the nanoFET having a source, a drain, and a gate, the first antibody disposed over the gate;
    applying a sample including the target protein to the device, the first antibody having affinity for the target protein;
    applying a plurality of types of additional antibodies, each type of additional antibody of the plurality of types of additional antibodies associated with a charge label having different charge than each other type of additional antibody of the plurality of types of additional antibodies, the plurality of types of antibodies including a second, the second antibody having affinity for the target protein, the target protein attaching to the first antibody and the second antibody attaching to the target protein to form an antibody assembly;
    detecting with the nanoFET the presence of the antibody assembly; and
    identifying the target protein based on a charge detected by the nanoFET and associated with the antibody assembly including the second antibody.

2. The method of claim 1, wherein the target protein and the second antibody bind before the protein binds with the first antibody.

3. The method of claim 1, wherein the target protein and the second antibody bind after the protein binds with the first antibody.

4. The method of claim 1, wherein the device further includes two charge electrodes, the method further comprising applying a DC voltage to the charge electrodes to push the second antibody toward the nanoFET.

5. The method of claim 4, wherein the DC voltage is in a range of 0.1 V/cm to 100 V/cm.

6. The method of claim 1, wherein the device further includes two charge electrodes, the method further comprising applying a AC voltage to the charge electrodes to push the second antibody toward the nanoFET.

7. The method of claim 6, further including applying a DC voltage with the AC voltage.

8. The method of claim 6, wherein the AC voltage is in a range of 0.1 V/cm to 100 V/cm.

9. The method of claim 1, wherein the plurality of types of additional antibodies includes a third antibody, the third antibody having a charge label different from the charge label of the second antibody.

10. The method of claim 1, wherein the sample in the well includes another target protein, a third antibody of the plurality of types of additional antibodies having a charge label different from the charge label of the second antibody, the method further including detecting a second molecular assembly including the first antibody attached to the another target protein attached to the third antibody.

11. A method of detecting a target protein, the method comprising:
  attaching antibodies to sensor surfaces of a device, the device having a plurality of nanoFETs, each nanoFET of the plurality of nanoFETs disposed in a separate well of a plurality of wells, each nanoFET having a source, a drain, and a gate, a sensor surface of the sensor surfaces disposed over the gate;
  applying a sample including the target protein to the device;
  applying a plurality of types of charge labeled antibodies to the device, each type of charge labeled antibody of the plurality of types of charge labeled antibodies having a different charge label, the target protein attaching to an antibody attached to the sensor surface and a charge labeled antibody of a type of charge labeled antibody of the plurality of types of charge labeled antibodies attaching to the target protein to form an antibody assembly;
  detecting with the nanoFET a charge of the antibody assembly; and
  identifying the target protein based on the charge of the antibody assembly.

12. The method of claim 11, wherein the target protein and the charge labeled antibody bind before the protein binds with the antibody attached to the sensor surface.

13. The method of claim 11, wherein the target protein and the charge labeled antibody bind after the protein binds with the antibody attached to the sensor surface.

14. The method of claim 11, wherein the device further includes two charge electrodes, the method further comprising applying a DC voltage to the charge electrodes to push the charge labeled antibody toward the nanoFET.

15. The method of claim 14, wherein the DC voltage is in a range of 0.1 V/cm to 100 V/cm.

16. The method of claim 11, wherein the device further includes two charge electrodes, the method further comprising applying a AC voltage to the charge electrodes to push the charge labeled antibody toward the nanoFET.

17. The method of claim 16, further including applying a DC voltage with the AC voltage.

18. The method of claim 16, wherein the AC voltage is in a range of 0.1 V/cm to 100 V/cm.

19. The method of claim 11, wherein the sample includes a second target protein, the second target protein attaching to a second charge labeled antibody of a second type of charge labeled antibody of the plurality of types of charge labeled antibodies, the second target protein binding to the antibody on a second sensor surface associated with a second nanoFET in a second well to form a second antibody assembly, the method further including detecting with the second nanoFET a second charge of the of the second charge assembly and identifying the second target protein based on the second charge of the second antibody assembly.

* * * * *

UNITED STATES PATENT AND TRADEMARK OFFICE
CERTIFICATE OF CORRECTION

| | | |
|---|---|---|
| PATENT NO. | : 10,180,428 B2 | Page 1 of 1 |
| APPLICATION NO. | : 14/864372 | |
| DATED | : January 15, 2019 | |
| INVENTOR(S) | : Oldham et al. | |

It is certified that error appears in the above-identified patent and that said Letters Patent is hereby corrected as shown below:

In the Claims

Column 16, Line 35 should read as follows:
"ing a second antibody, the second antibody having affinity for the"

Signed and Sealed this
Eleventh Day of February, 2020

Andrei Iancu
*Director of the United States Patent and Trademark Office*